(12) United States Patent
Hamada et al.

(10) Patent No.: US 9,846,215 B2
(45) Date of Patent: Dec. 19, 2017

(54) MRI EMBODIMENTS FOR CONTROLLING AN ARRANGEMENT ORDER OF MULTIPLE ECHOES IN A K-SPACE

(71) Applicant: HITACHI, LTD., Tokyo (JP)

(72) Inventors: Munesato Hamada, Tokyo (JP); Shouichi Miyawaki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 464 days.

(21) Appl. No.: 14/413,796

(22) PCT Filed: Aug. 20, 2013

(86) PCT No.: PCT/JP2013/072128
§ 371 (c)(1),
(2) Date: Jan. 9, 2015

(87) PCT Pub. No.: WO2014/030621
PCT Pub. Date: Feb. 27, 2014

(65) Prior Publication Data
US 2015/0204960 A1    Jul. 23, 2015

(30) Foreign Application Priority Data

Aug. 22, 2012  (JP) .................................. 2012-183371

(51) Int. Cl.
*G01R 33/561* (2006.01)
*A61B 5/055* (2006.01)
(Continued)

(52) U.S. Cl.
CPC .......... *G01R 33/5615* (2013.01); *A61B 5/055* (2013.01); *G01R 33/385* (2013.01);
(Continued)

(58) Field of Classification Search
CPC .............. G01R 33/5615; G01R 33/385; G01R 33/4818; G01R 33/543; G01R 33/5617; A61B 5/055
See application file for complete search history.

(56) References Cited

U.S. PATENT DOCUMENTS 5,378,985 A * 1/1995 Hinks .............. G01R 33/56554
324/307
6,369,568 B1 * 4/2002 Ma ................... G01R 33/56554
324/307
(Continued)

FOREIGN PATENT DOCUMENTS

| JP | 5-253202 A | 10/1993 |
|----|-----------|---------|
| JP | 2003-235826 A | 8/2003 |
| JP | 2006-304955 A | 11/2006 |

*Primary Examiner* — G. M. Hyder

(57) ABSTRACT

To avoid discontinuities between echoes from becoming large level differences in a k-space and to reduce artifacts generated in a reconstructed image due to the discontinuities in the k-space, an MRI apparatus of the present invention uses phase characteristics of multiple echoes to be collected after a single RF excitation to control an arrangement order in the k-space where the multiple echoes are arranged when a pulse sequence of the fast spin echo method that collects the multiple echoes using a spin flip after a single RF excitation is executed. The arrangement is controlled so that echoes with small phase errors between the echoes at least near the center of the k-space are adjacent to each other.

13 Claims, 14 Drawing Sheets

(51) Int. Cl.
*G01R 33/385* (2006.01)
*G01R 33/48* (2006.01)
*G01R 33/54* (2006.01)
G01R 33/565 (2006.01)

(52) U.S. Cl.
CPC ....... *G01R 33/4818* (2013.01); *G01R 33/543* (2013.01); *G01R 33/5617* (2013.01); *G01R 33/4824* (2013.01); *G01R 33/546* (2013.01); *G01R 33/5659* (2013.01); *G01R 33/56572* (2013.01)

(56) References Cited

U.S. PATENT DOCUMENTS

2007/0063704 A1* 3/2007 Peters .............. G01R 33/56554
324/309
2009/0124885 A1* 5/2009 Umeda .................. A61B 5/055
600/410
2010/0260403 A1* 10/2010 Takizawa ............... A61B 5/055
382/131

* cited by examiner

FIG.3
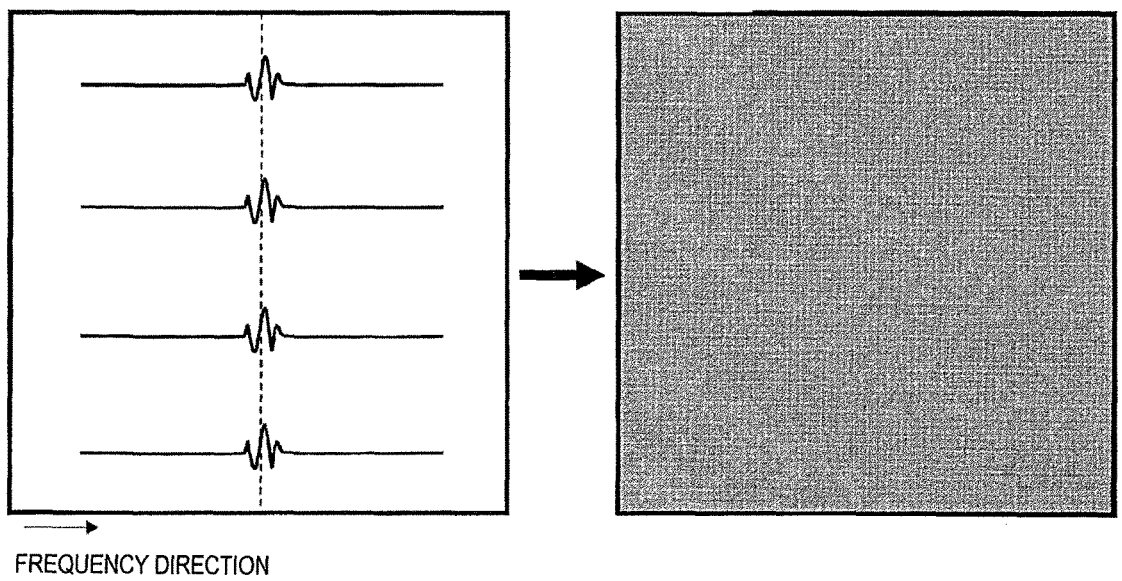
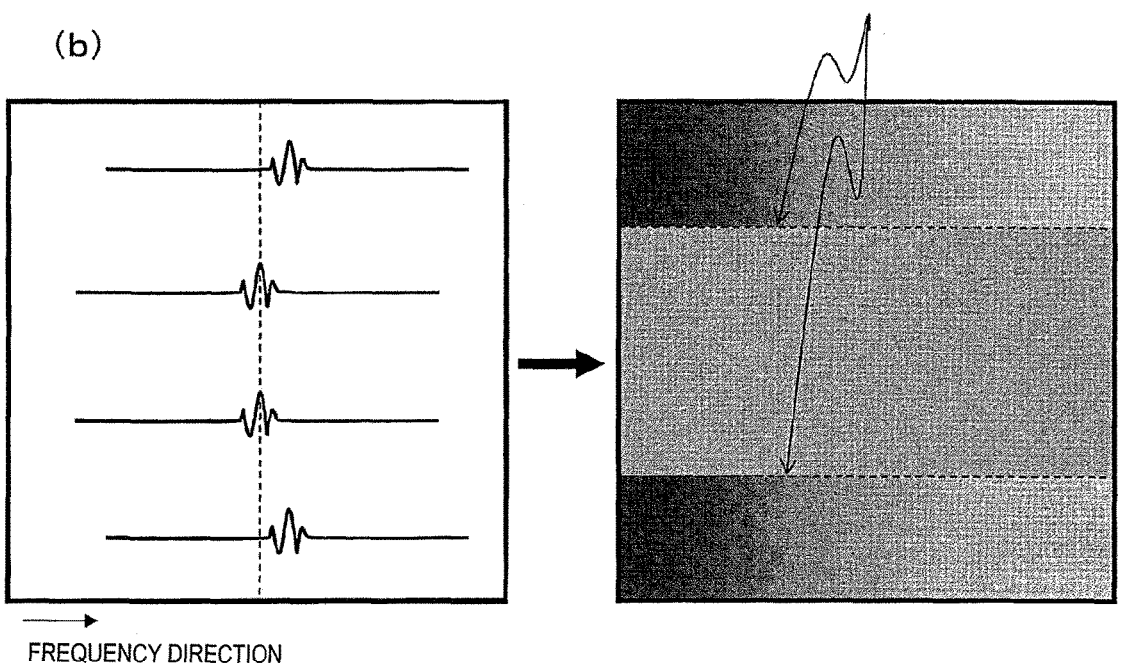

FIG.8
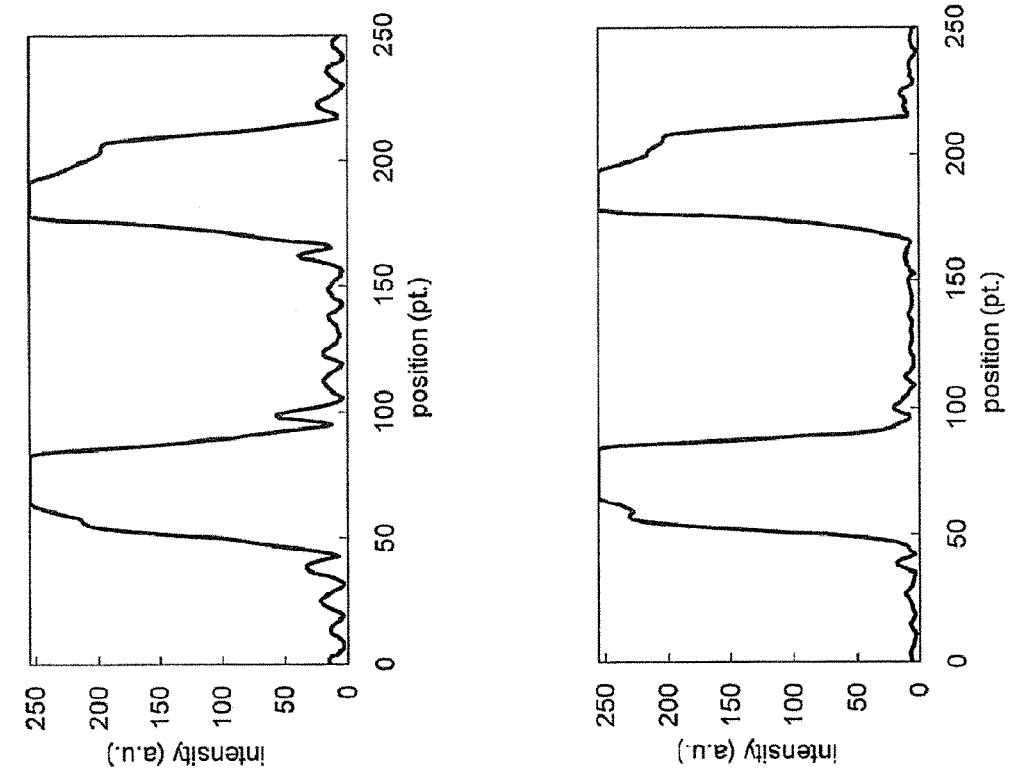
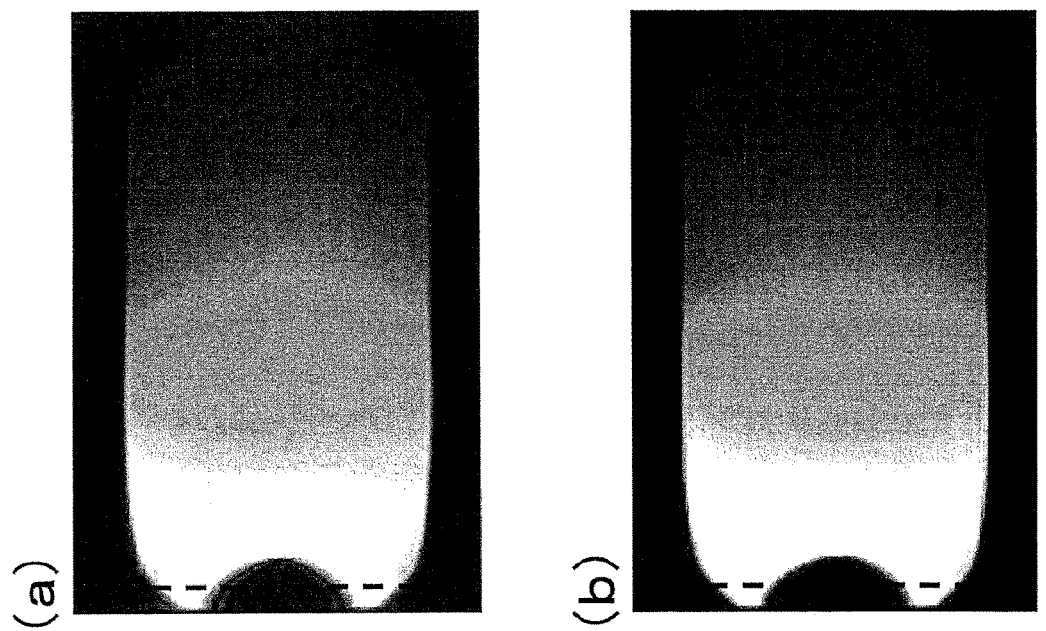

FIG.11
(a) 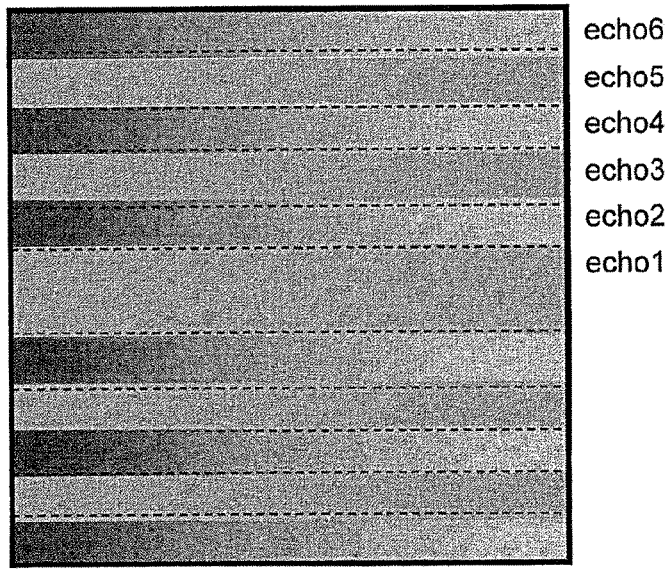
echo6
echo5
echo4
echo3
echo2
echo1
(b) 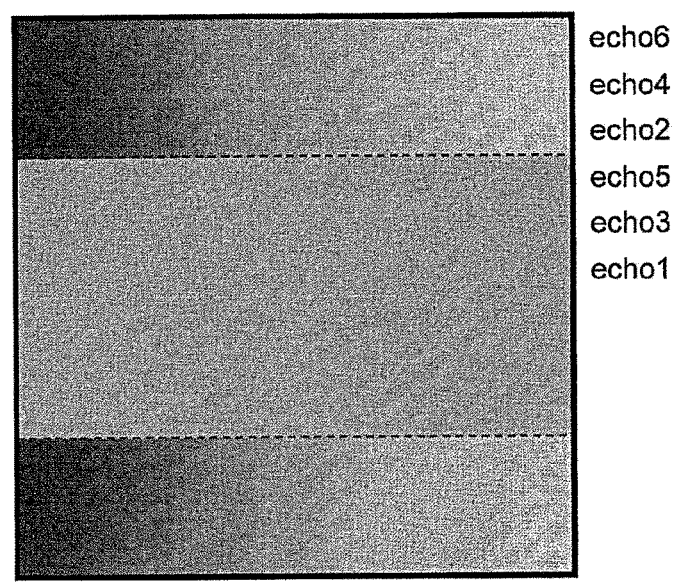
echo6
echo4
echo2
echo5
echo3
echo1

MRI EMBODIMENTS FOR CONTROLLING AN ARRANGEMENT ORDER OF MULTIPLE ECHOES IN A K-SPACE

TECHNICAL FIELD

This invention relates to a technique for eliminating an influence of an error magnetic field included in each echo collected continuously after a single RF excitation in an magnetic resonance imaging apparatus (hereinafter, referred to as an MRI apparatus) equipped with an pulse sequence based on the fast spin echo method.

BACKGROUND ART

In an MRI apparatus, various pulse sequences are used corresponding to the imaging target and image type. Among those pulse sequences, a pulse sequence referred to as the fast spin echo method (FSE method) is widely used due to the short imaging time and the diversity of image types that can be imaged.

In the FSE method, using a plurality of 180-degree RF pulses, a plurality of spin echoes are obtained by repeatedly inverting an echo generated after one spin excitation by a 90-degree RF pulse. Highly accurate control is required for an RF pulse to generate these echoes and a gradient magnetic field pulse that encodes echoes. In a pulse sequence that is software to achieve the FSE method, an intensity and a timing of an ideal RF pulse and a gradient magnetic field pulse are described. However, since errors actually occur for a gradient magnetic field pulse and an RF pulse generated by hardware, it is difficult to achieve a theoretical pulse sequence in a static magnetic field space. Therefore, each echo will include a magnetic field error, and artifacts occur in an image that uses such an echo.

Various improvement measures have been proposed for this problem. For example, in the Non-patent Literature 1 and Patent Literature 1, a method is proposed that collects raw data itself in a state close to an ideal as possible by obtaining reference data by pre-scan to adjust a pulse sequence using the results. Specifically, this method measures a first echo and a second echo by pre-scan that uses a modified FSE pulse sequence where a phase encoding is not used in the first step, calculates a phase error between these echoes, and adjusts a 180-degree RF pulse so that the phase error is minimized. Next, as the second step, this method calculates a difference between gradients of phase profiles of a first echo and a second echo measured by pre-scan similarly and corrects a read gradient magnetic field so that the phase error is minimized.

CITATION LIST

Patent Literature

PTL 1: Description of U.S. Pat. No. 5,378,985

Non-Patent Literature

NPL 1: R. Scott Hinks etc., "Fast Spin Echo Prescan for Artifact Reduction", Soc. Magn. Reson. Abstract, 1995; 3: 634

SUMMARY OF INVENTION

Technical Problem

As described above, since the technique adjusting a pulse sequence itself performs the same adjustment assuming that a certain error occurs for all the echoes of an echo train, for, example, the technique cannot handle a case where a different error occurs for each echo in the echo train. Also, in order to perform a highly accurate adjustment, pre-scans need to be repeated, which results in an extension of imaging time.

Also, although an error occurred for an echo includes a different error component depending on a position of an imaging space (real space) where an imaging object is placed, the echo itself is a signal generated from the whole excitation area of the imaging object and cannot separate the different error component depending on the position.

Even if the error component can be measured, it is difficult to locally change a gradient magnetic field and spatial distribution of RF and to address the different error component depending on the position.

Even in a case where each echo in an echo train has a different error, the present invention avoids that discontinuities among echoes become large in a k-space as possible and has a problem to reduce artifacts generated in a reconstruction image by the discontinuities in the k-space.

Solution to Problem

In order to solve the above problem, an MRI apparatus of the present invention controls an arrangement order in a k-space where multiple echoes are arranged using phase characteristics of the multiple echoes to be collected after a single RF excitation when a control unit that controls imaging by controlling a high-frequency magnetic field generating unit, a gradient magnetic field generating unit, and a reception unit executes a pulse sequence of the fast spin echo method where multiple echoes are collected using spin inversion after a single RF excitation. The arrangement control is performed so that echoes with a smaller phase error among echoes are adjacent each other at least in the vicinity of the center of the k-space.

Phase characteristics of each echo can be obtained by pre-measurement. For the pre-measurement, a pulse sequence of the fast spin echo method that does not use phase encoding can be used. Instead of the pre-measurement, the phase characteristics specific to a fast spin echo can also be used.

Advantageous Effects of Invention

By controlling an arrangement order in a k-space for each echo of an echo train, magnetic field errors inherent in the respective echoes can be dispersedly arranged in the k-space, which can solve a problem of image blurring caused by phase errors among echoes (discontinuities of the k-space) based on the magnetic field errors and phase error accumulation.

BRIEF DESCRIPTION OF DRAWINGS

FIG. 3 is a diagram describing phase errors to be targets of an MRI apparatus of the present invention, shows a state where there is no phase error for each echo in (a), and shows a state where a phase error occurs in (b). The right-side diagram and the left-side diagram respectively show the k-space data and the data after the Fourier transform is performed for the k-space data in a frequency direction.

FIG. 8 is a diagram showing an effect of arrangement order control by the first embodiment. (a) is a case where the arrangement order control is not performed, and (b) is a case where the arrangement order control is performed.

FIG. 11 is a diagram describing the k-space arrangement order control in the second embodiment. (a) shows a k-space arrangement by general centric ordering, and (b) shows a k-space arrangement by the second embodiment.

DESCRIPTION OF EMBODIMENTS

Hereinafter, the embodiments of the present invention will be described referring to diagrams. First, an overview of an MRI apparatus to which the present invention is applied and a pulse sequence of the fast spin echo method (FSE method) to be executed in the MRI apparatus will be described referring to FIGS. 1 and 2.

Figure 1:
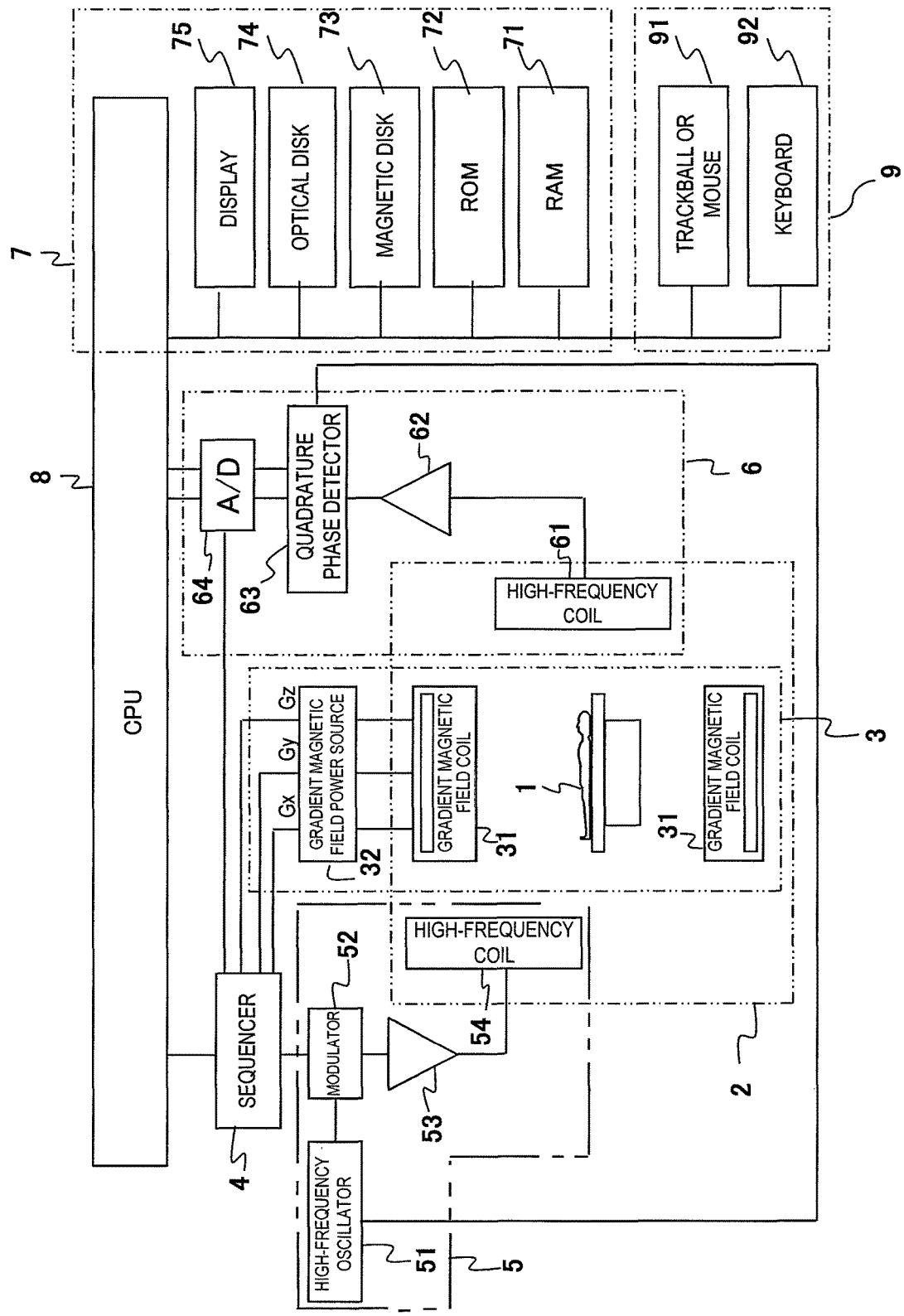
FIG. 1 is a block diagram showing an overall configuration of an MRI apparatus to which the present invention is applied.

The MRI apparatus shown in FIG. 1 is mainly comprised of the static magnetic field generating magnetic circuit 2, the gradient magnetic field generating unit 3, the transmission unit 5, the reception unit 6, the signal processing unit 7, the sequencer 4, the central processing unit (CPU) 8, and the operation unit (user interface unit) 9.

The static magnetic field generating magnetic circuit 2 is to generate a homogeneous static magnetic field in a space in which the object 1 is placed, and although not shown in the diagram, a magnetic field generating unit of the permanent magnetic method, the normal conduction method, or the superconductive method is disposed. Depending on the orientation of a static magnetic field, there are the horizontal magnetic field method parallel to the body axis of an object and the vertical magnetic field method orthogonal to the body axis.

The gradient magnetic field generating unit 3 is comprised of the gradient magnetic field coils 31 wound in the three axis directions of X, Y, and Z as well as the gradient magnetic field power source 32 driving the respective coils and can apply the gradient magnetic fields Gs, Gp, and Gf in arbitrary three axis directions to the object 1 by driving the gradient magnetic field power source 32 of the respective coils according to the command from the sequencer 4. By the manner of applying the gradient magnetic fields, a slice surface to the object 1 can be set, and an echo is also encoded to provide position information.

The transmission unit 5 is to irradiate a high-frequency signal in order to generate a nuclear magnetic resonance in atomic nuclei of the atoms comprising the biological tissues of the object 1 by a high-frequency magnetic field pulse to be transmitted from the sequencer 4, is comprised of the high-frequency oscillator 51, the modulator 52, the high-frequency amplifier 53, and the high-frequency coil 54 on the transmission side, and irradiates an electromagnetic wave (high-frequency signal) to the object 1 by supplying a high-frequency pulse output from the high-frequency oscillator 51 to the high-frequency coil 54 on the transmission side disposed in the vicinity of the object 1 after the high-frequency pulse is amplified by the high-frequency amplifier 53.

The reception unit 6 is to detect an echo (NMR signal) emitted by nuclear magnetic resonance of atomic nuclei in the biological tissues of the object 1; is comprised of the high-frequency coil 61 on the reception side, the amplifier 62, the quadrature phase detector 63, and the A/D converter 64; detects a responding electromagnetic wave (NMR signal) of the object 1 by an electromagnetic wave irradiated from the high-frequency coil 54 on the transmission side in the high-frequency coil 61 on the reception side disposed in the vicinity of the object 1; inputs the electromagnetic wave in the A/D converter 64 via the amplifier 62 and the quadrature phase detector 63 to convert the electromagnetic wave into a digital quantity; and additionally transmits it to the signal processing unit 7 as two-series collection data sampled by the quadrature phase detector 63 at a timing commanded from the sequencer 4.

The signal processing unit 7 is to perform image reconstruction calculation using an echo detected in the reception unit 6 as well as to display images and is comprised of the CPU 8 performing processes such as the Fourier transform, correction coefficient calculation, and image reconstruction for echoes and controlling the sequencer 4, the memory units 71 (RAM) and 72 (ROM), the data storage units 73 (magnetic disk) and 74 (optical disk), and the display 75. The memory units are comprised of the ROM (Read-Only Memory) 72 memorizing invariable parameters etc. to be used for a program for performing time-sequential image analysis processing and measurement as well as the execution; the RAM (Random-Access Memory) 71 memorizing a measured parameter obtained in pre-measurement, an echo detected in the reception unit 6, a parameter for temporarily storing images to be used for setting a region of interest as well as setting the region of interest, etc.; and so on. The data storage units are to record image data reconstructed in the CPU 8 and are comprised of, for example, the optical disk 74, the magnetic disk 73, etc. The display 75 visualizes image data read out from the magnetic disk 73 or the optical disk 74 to display it as a tomographic image.

The sequencer 4 is a control unit to apply a high-frequency magnetic field pulse and a gradient magnetic field pulse that are required for imaging according to a predetermined pulse sequence, operates by control of the CPU 8, and transmits various commands required for data collection of MR images to the transmission unit 5, the gradient magnetic field generating unit 3, and the reception unit 6. Also, the operation unit 9 is a user interface to input control information of processes that the signal processing unit 7 performs and is comprised of an input unit and a display unit such as a trackball, the mouse 91, and the keyboard 92. A display installed on the signal processing unit 7 can be used also as a display unit of the operation unit 9.

Next, a pulse sequence that the MRI apparatus executes will be described. There are various pulse sequences corresponding to various imaging methods. The pulse sequences are memorized in a memory unit as programs and are read out and executed by the sequencer 4 along with a parameter memorized in the memory unit and a parameter set by a user for imaging. In the respective embodiments of the present invention, the pulse sequence of the FSE method will be executed as one of such pulse sequences.

Figure 2:
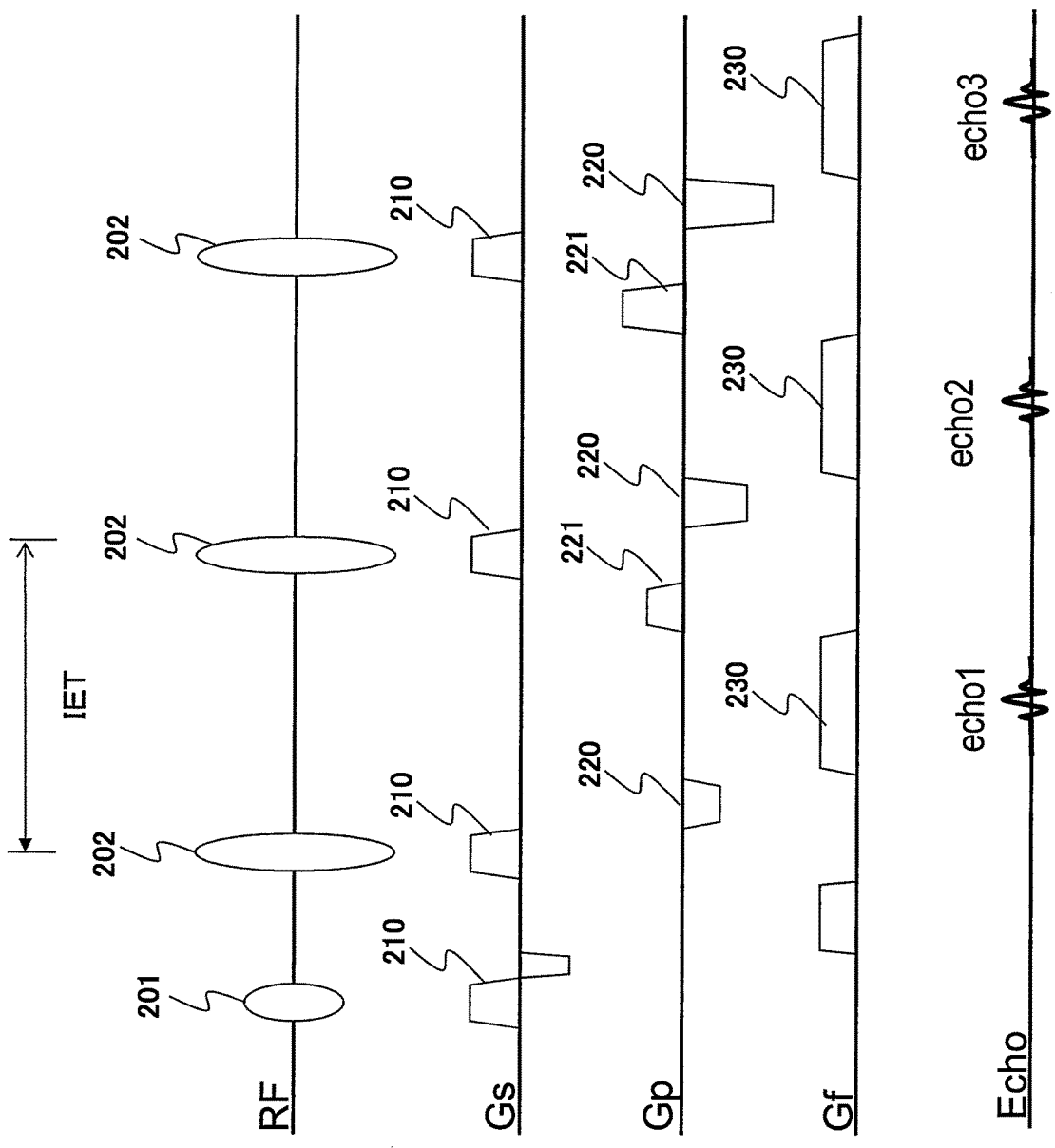
FIG. 2 is a diagram showing a basic pulse sequence of the FSE method to be executed in an MRI apparatus of the present invention.

A basic 2D pulse sequence of the FSE method is shown in FIG. 2. In this pulse sequence, as shown in the diagram, the RF pulse 201 that excites a nuclear spin and a normal proton in the object 1 is applied to the object 1. For example, a flip angle of the RF pulse 201 is 90 degrees, and hereinafter, the RF pulse 201 is referred to as an excitation RF pulse or a 90-degree RF pulse. After the 90-degree RF pulse 201 is applied to the object 1, the RF pulse 202 that inverts an excitation spin at the timing of TE/2 for an echo time TE is applied to the object 1. The RF pulse 202 is referred to as an inversion pulse or a 180-degree RF pulse. After the 180-degree RF pulse is applied, the echo echo1 from the object 1 is collected at a time point where the time TE/2 has elapsed.

Hereinafter, the 180-degree RF pulses are applied to the object 1 at the same time interval IET to measure the echoes echo2, echo3, and more from the object 1 among the 180-degree RF pulses. Additionally, in FIG. 2, although the three typical 180-degree RF pulses are shown, the number of 180-degree RF pulses can be set arbitrarily in spin longitudinal relaxation time, echoes of all-phase encoding can also be measured (single shot) after one excitation RF pulse, and the echoes of all-phase encoding can also be measured (multi-shot) after multiple excitation RF pulses are repeated. A group of echoes to be collected after one excitation is referred to as an echo train.

Also, in the pulse sequence of FIG. 2, as a gradient magnetic field, the gradient magnetic field Gs210 selecting a slice is applied when the RF pulses 201 and 202 are applied, and then the gradient magnetic field Gf230 in a frequency-encoding direction is applied when an echo is measured. Additionally, the gradient magnetic field Gp220 where phase encoding is performed for each echo and the gradient magnetic field Gp221 for rephasing are applied. In case of 3D imaging, gradient magnetic field application that performs encoding for the axis in a slice selection direction is added. Also, in radial scanning where a k-space is scanned radially, gradient magnetic fields in the phase-encoding direction and the frequency-encoding direction are combined to encode and read out an echo.

Additionally, not shown in FIG. 2, a certain spin, for example, such as a pre-pulse saturating spins of adipose tissues, an IR pulse to invert, etc. can be added before a 90-degree RF pulse.

The k-space data are echoes (sampling data) that are measured by executing such a pulse sequence and arranged in a memory space. Using the 2D pulse sequence shown in FIG. 2 for a simple description, the k-space is a two-dimensional flat surface whose horizontal and vertical axes are in the frequency-encoding direction and in the phase-encoding direction respectively, the arrangement order in the k-space is determined by a phase-encoding amount provided for each echo in the pulse sequence, that is, an intensity of a phase-encoding gradient magnetic field to be applied. In the pulse sequence shown in FIG. 2, the arrangement order is the centric order, a phase-encoding amount increases by a predetermined increment in order from the first echo after an RF excitation. Hence, echoes are arranged in order from the center of the k-space toward a high-frequency region. An MRI apparatus of the present invention is characterized by the arrangement order in the k-space, that is, adjusting application steps of an encoding gradient magnetic field to be applied to each echo in an echo train.

Based on the configuration of the MRI apparatus described above and a pulse sequence to be executed by the MRI apparatus, the respective embodiments of the present invention will be described.

First Embodiment

In an MRI apparatus of the present embodiment, a control unit controls an arrangement order in a k-space in which multiple echoes are arranged using phase characteristics of multiple echoes to be collected after a single RF excitation. An arrangement order of echoes in a k-space is controlled via control of an application amount of a phase-encoding gradient magnetic field. The control unit is comprised of a pre-measurement unit to measure phase characteristics of multiple echoes and a phase calculation unit calculating difference between phases of the multiple echoes obtained by the pre-measurement unit and a reference phase as well as determining an arrangement order to arrange the multiple echoes in an ascending order of phase differences from the reference phase. For example, a phase value of an echo to be collected first after an RF excitation can be used as a reference phase. Alternatively, an average value of multiple echo phases to be collected after a single RF excitation can be used as a reference phase.

An arrangement order is to be controlled by arranging multiple echoes measured in a pulse sequence of the FSE method in a k-space according to the arrangement order determined by the phase calculation unit. For example, an echo to be collected first after an RF excitation can be arranged in the center of the k-space or a position closest to the center, and the second and subsequent echoes can be arranged in the k-space according to the arrangement order determined by the phase calculation unit.

First, a magnetic field error of an echo that is to be a target of an MRI apparatus of the present invention will be described.

In a pulse sequence as shown in FIG. 2, the respective echoes to be collected each time a 180-degree RF pulse is inverted will include errors different for each echo because of a measurement timing where a 90-degree RF pulse application is specified as the origin and different inversion times of a 180-degree RF pulse. Such errors includes application amount errors of a gradient magnetic field pulse and an RF pulse accumulated in a pulse sequence before a measurement, an error caused by a unnecessary magnetic field due to an eddy current, etc. Normally, echoes are controlled so that the intensity reaches the maximum at the center of a frequency encoding gradient magnetic field, and in a k-space where these echoes are arranged, as shown in the left diagram of FIG. 3(*a*), the echo peaks are located in the center of the frequency encoding direction in the k-space. Performing the Fourier transform for such k-space data in a frequency encoding direction to convert it into phase information, as shown in the right diagram of (a), the phase becomes homogeneous over the whole k-space.

However, if echoes have errors such as described above, positions of echo peaks for a frequency encoding gradient magnetic field differs, and as shown in FIG. 3(*b*), k-space data will include echoes whose echo peaks are shifted from the center of the frequency encoding direction. When the Fourier transform is performed for such k-space data in a frequency encoding direction, phase inclinations vary depending on the echo, and discontinuities occur between echoes. A phase error (D of each echo can be expressed in the general formula (1).

[Number 1]

$$\phi = \phi_0 + \phi_1 r + \phi_2 r^2 + \quad (1)$$

In the formula, r is a distance from the center of a gradient magnetic field, $\phi_0$ is a phase error (zero-order error) independent of a position, $\phi_1 r$ is a phase error primarily dependent on a distance, and $\phi_2 r^2$ is a phase error secondarily dependent on a distance.

Of the above errors, although it is relatively easy to remove zero-order errors occurring to all the echoes, that is, offset errors by adjusting a pulse sequence, errors that occur to the second and subsequent echoes as well as accumulate cannot be solved easily only by adjusting the pulse sequence.

The present embodiment controls an echo arrangement order in a k-space for errors accumulated for each echo and differing depending on the echo and errors occurring depending on the position in an imaging space targeted for imaging to disperse or average errors in the k-space, which obtains the same effect as a state where the errors are removed substantially.

Figure 4:
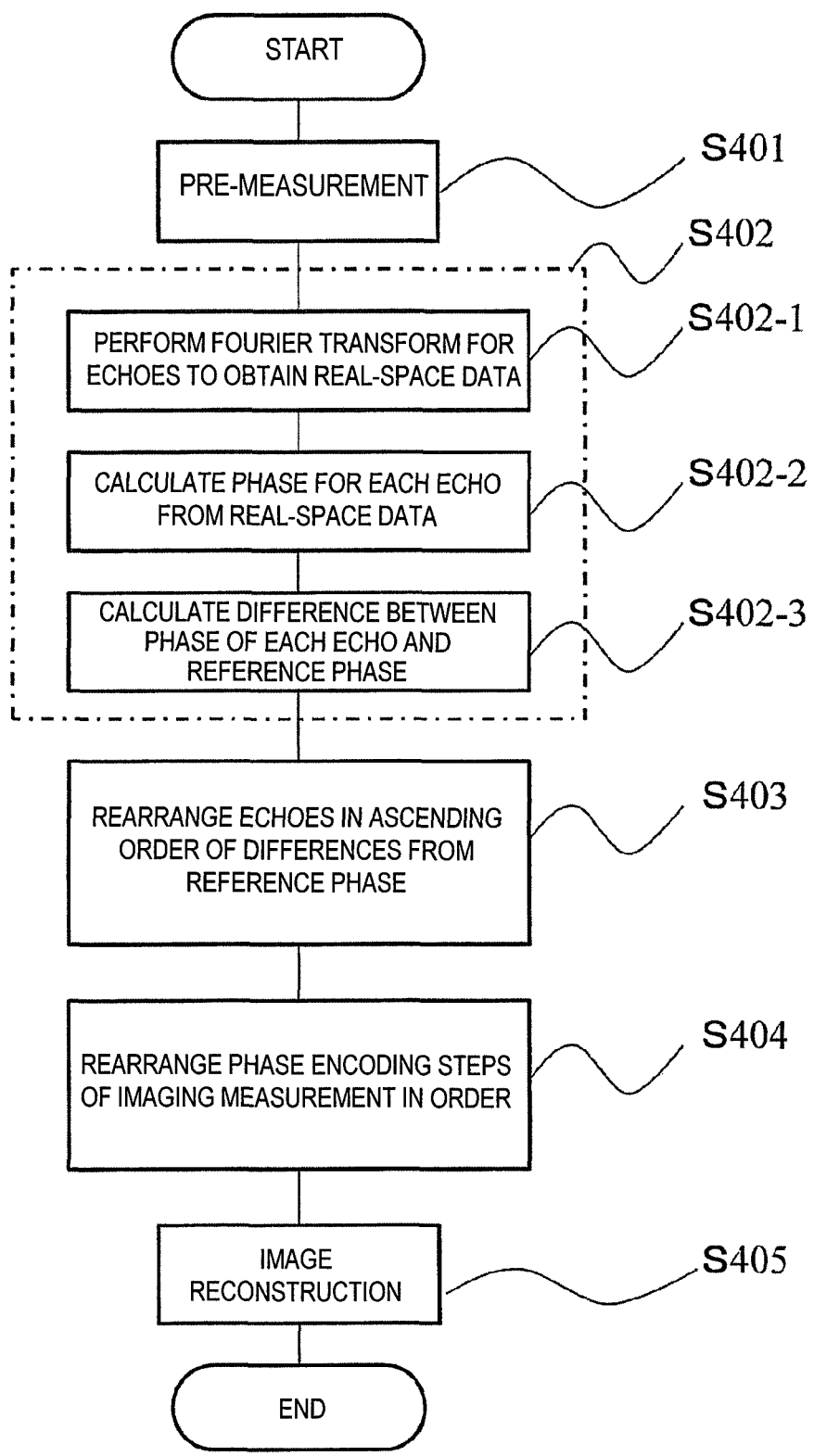
FIG. 4 is a flow diagram showing a processing procedure of a control unit of the first embodiment.
Figure 5:
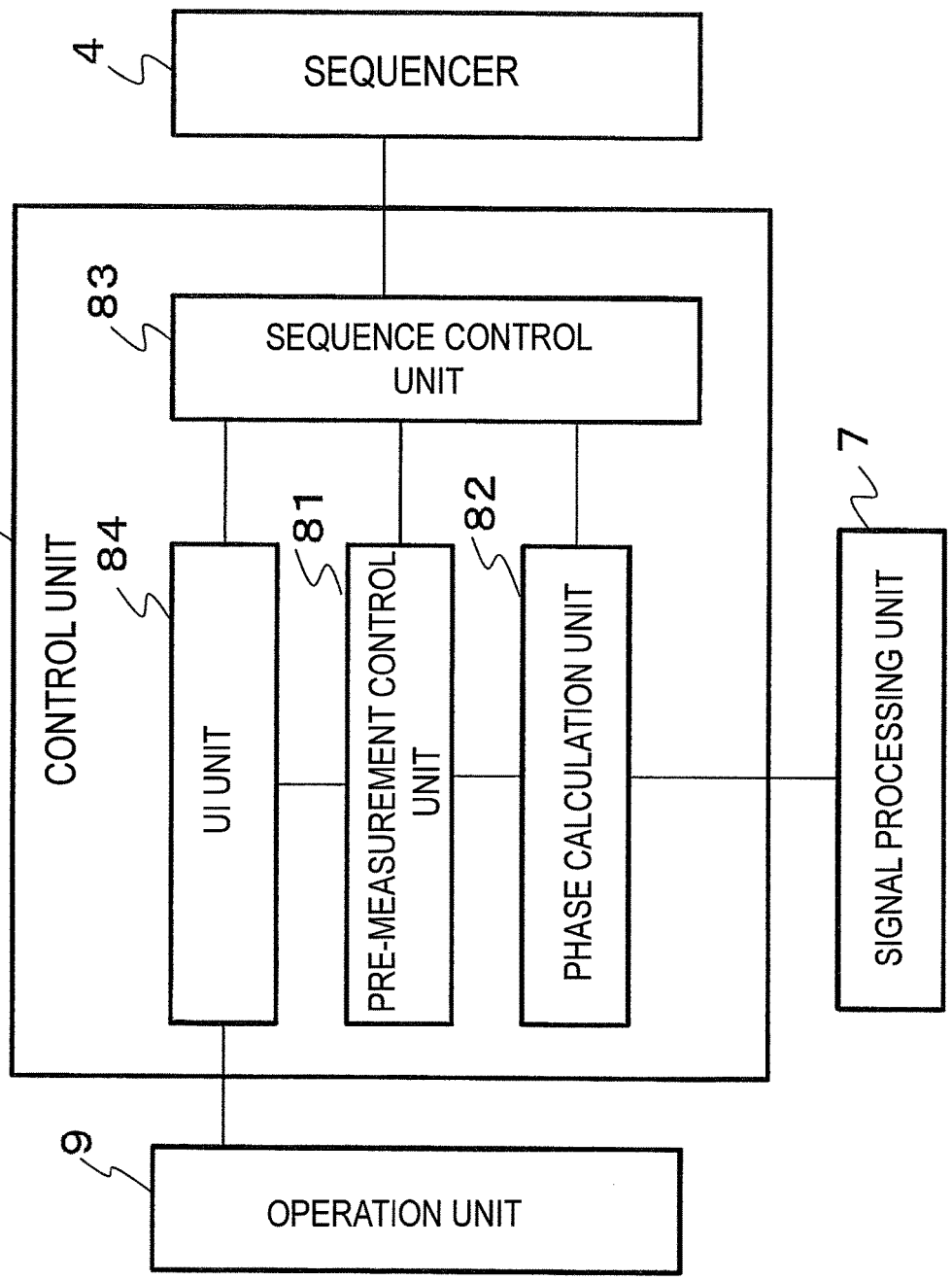
FIG. 5 is a functional block diagram of a control unit of the first embodiment.

The processing procedure and the functional block diagram of a control unit (CPU8) controlling an echo arrangement order in a k-space are shown in FIGS. 4 and 5.

As shown in FIG. 5, the control unit 80 is comprised of the pre-measurement control unit 81, the phase calculation unit 82, the sequence control unit (arrangement order control unit) 83, and the user interface unit (UI unit) 84. The pre-measurement control unit 81 determines a pulse sequence of predetermined pre-measurement according to a command from the UI unit 84 and transmits a command to perform the pre-measurement to the sequencer 4 via the sequence control unit 83. The phase calculation unit 82 uses echoes obtained in the pre-measurement to determine a k-space arrangement order of echoes to be obtained during imaging measurement. The pre-measurement control unit 81 and the phase calculation unit 82 are units (phase characteristics obtaining units) to obtain phase characteristics of each echo in a pulse sequence based on the FSE method. The sequence control unit 83 determines pulse sequences of pre-measurement and imaging measurement and transmits a command to execute the pre-measurement and imaging measurement to the sequencer 4 according to the determined pulse sequence.

In the present embodiment, an arrangement order for which phase characteristics of each echo are considered is controlled based on a case where the arrangement order in a k-space is the centric order.

First, when a pulse sequence of the FSE method is selected as an imaging method, pre-measurement is performed to measure phase characteristics of echoes to be collected after a single RF excitation in the pulse sequence (Step S401).

Figure 6:
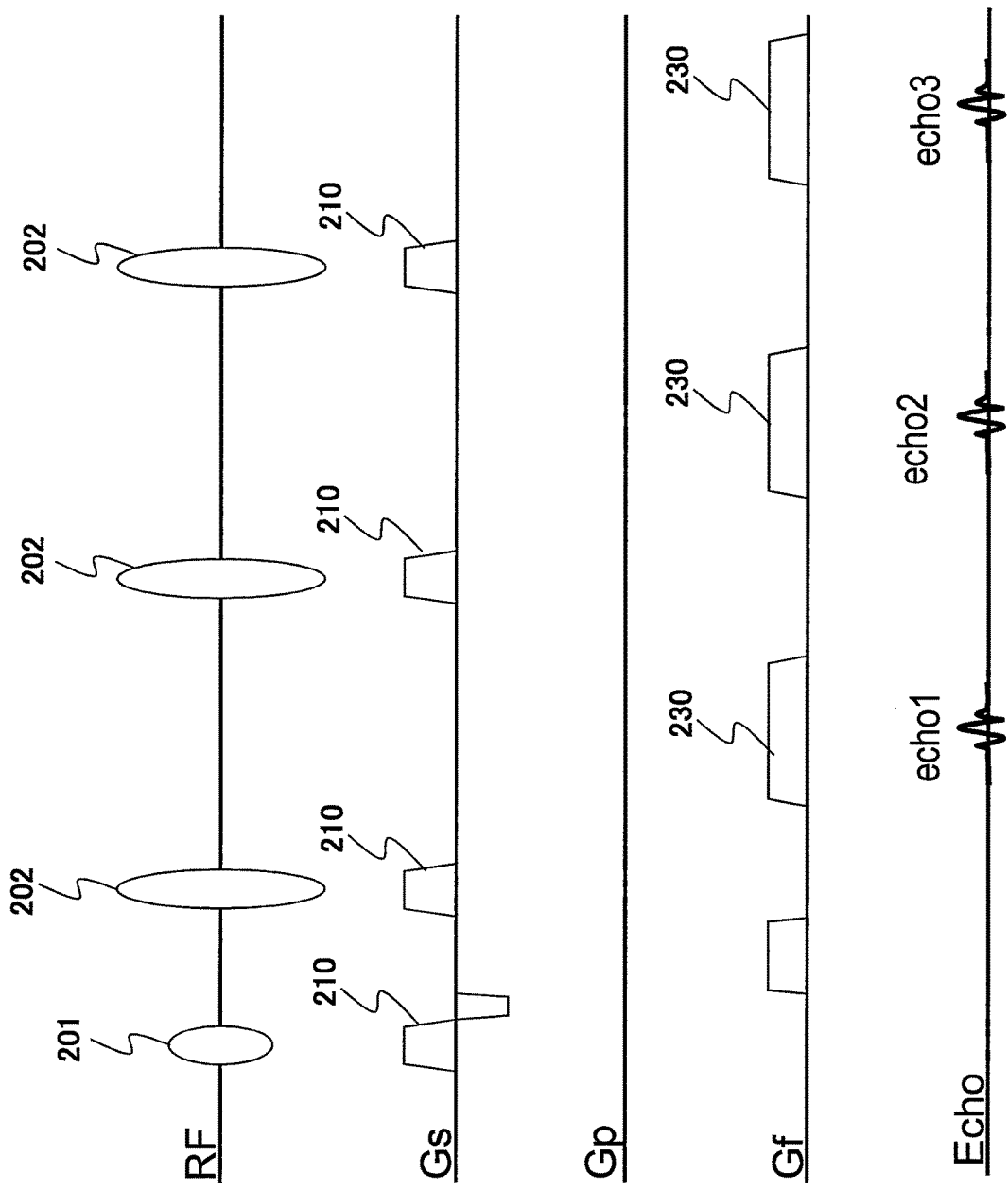
FIG. 6 is a diagram showing an example of a pulse sequence of pre-measurement in the first embodiment.

Although a pulse sequence of pre-measurement is that of the FSE method same as that of imaging (imaging measurement) to obtain an MR image of the object 1, a phase encoding gradient magnetic field is not applied. Therefore, in case of the 2D pulse sequence shown in FIG. 2, Gp can be omitted. An example of the pulse sequence of the pre-measurement is shown in FIG. 6. Therefore, each echo of the pre-measurement is collected in a condition where conditions other than phase encoding (a read-out gradient magnetic field pulse, an RF pulse, and influences of the other external magnetic fields) are the same as the pulse sequence of imaging measurement. Also, the pre-measurement may be performed only once, or it may be performed twice or more to add the results. The addition results in a trade-off between imaging time extension due to the pre-measurement and result accuracy improvement, and a user may perform the selection.

Next, phase characteristics of the multiple echoes echo1 to echoN (N is the number of echoes to be collected after one excitation=the number of echo trains) collected by the pre-measurement are calculated (Step S402). For this purpose, the Fourier transform is performed for the measured echoes in the frequency encoding direction to obtain data (x-ky hybrid data) converted into real space only in the frequency direction (Step S402-1). The hybrid data is complex data, and the real part and the imaginary part can be used to calculate an angle, that is, a phase (Step S402-2).

Of the multiple echoes, a phase of the echo echo1 to be collected first after excitation is specified as a reference phase, and phase differences between phases of the second and subsequent echoes echo2 to echoN and the reference phase are calculated (Step S402-3). The phase differences are phase characteristics of each echo.

Next, the multiple echoes are arranged in an ascending order of the phase difference (the absolute value) from the first echo. According to the order, an arrangement order of echoes in imaging measurement is determined (Step S403).

For example, if an echo with the smallest phase difference from the first echo is the fifth echo, a phase encoding gradient magnetic field of the fifth echo is set so that an echo to be collected fifth in imaging measurement is arranged next to the first echo in a k-space. Similarly, a phase encoding gradient magnetic field is set so that an echo (the n-th echo) where a phase difference from the first echo is the second smallest after the fifth echo is arranged next to the fifth echo in a k-space. Hence, k-space arrangement is configured so that phase differences between adjacent echoes are minimized.

Next, imaging measurement of the FSE method is executed (Step S404). In imaging measurement, pulse sequences are repeated by an increment (application step) of phase encoding in which echoes from the first to the n-th in an echo train are arranged in an arrangement order determined in Step S403 in a k-space to collect k-space data. Finally, the 2D Fourier transform is performed for the k-space data to reconstruct an image (Step S405).

Figure 7:
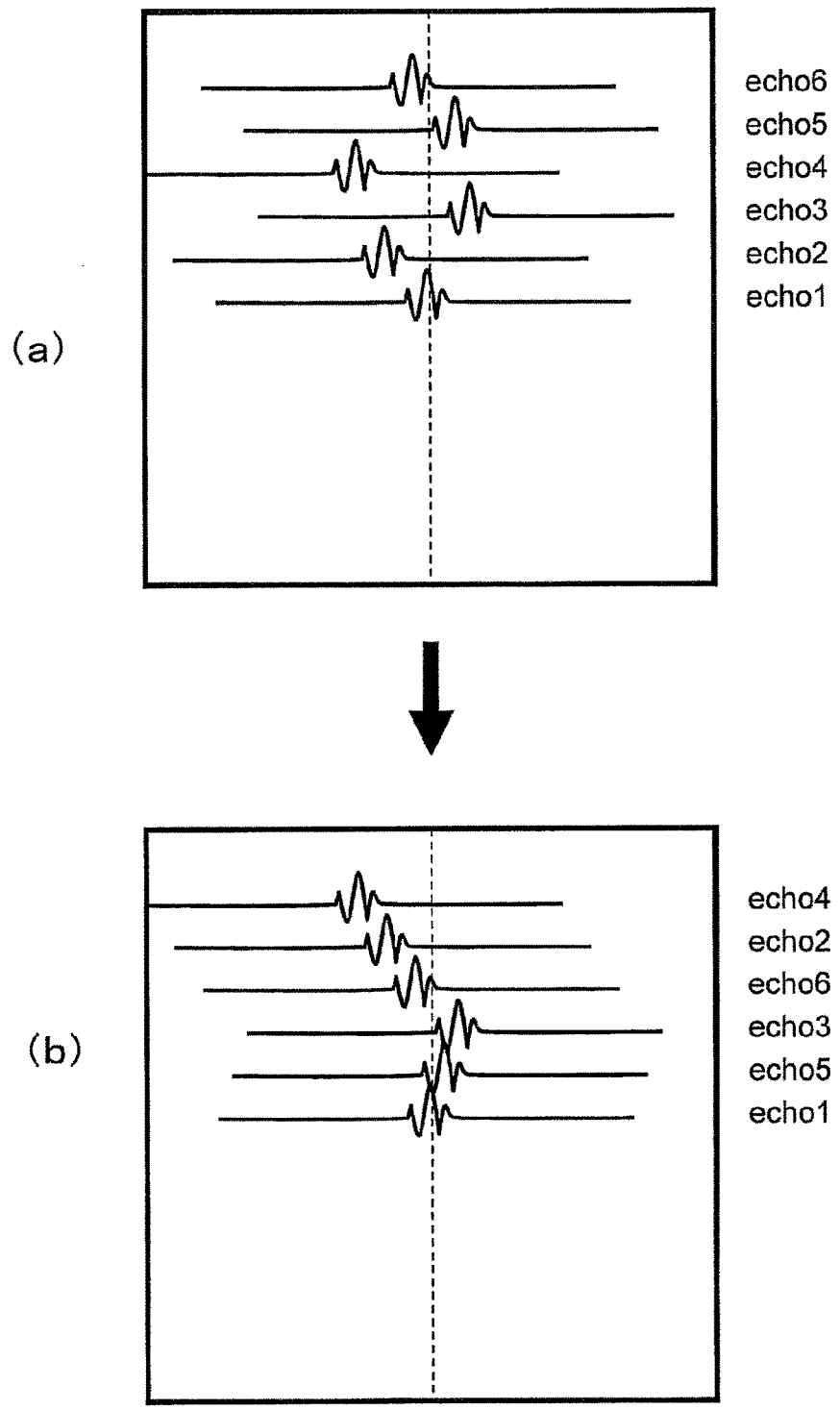
FIG. 7 is a diagram describing an effect of arrangement order control by the first embodiment. (a) is a case where the arrangement order control is not performed, and (b) is a case where the arrangement order control is performed.

The k-space data obtained by the above processes is shown schematically in FIG. 7(*b*). In a case where echoes in which phase errors exist for each echo are collected in a basic centric order without controlling a k-space arrangement order, as shown in FIG. 7(*a*), the echo-peak positions are not aligned. Although data after the Fourier transform is performed for such data in the frequency encoding direction differs in a phase inclination for each echo and causes discontinuity for each echo, phase differences become the smallest between adjacent echoes in case of controlling an arrangement order, which can minimize influence of discontinuities on an image. Hence, in an image obtained by performing the Fourier transform for k-space data, an image blur caused by a phase level difference between echoes is removed.

In FIGS. 8(*a*) and 8(*b*), the image (the left diagram of (b)) and the profile (the right diagram of (b)) obtain by the present embodiment as well as the image (the left diagram of (a)) and the profile (the right diagram of (a)) to which the present embodiment is not applied are shown. In FIGS. 8(*a*) and 8(*b*), the profiles in the right diagrams are those in positions shown with the dotted lines in the left diagrams. Although the small unevenness is generated in addition to the actual signals in the profile and becomes an excess signal in the image shown in FIG. 8(a), the unevenness almost disappears in an image of FIG. 8(b) where an arrangement order is controlled, and then the image quality is improved.

According to the present embodiment, phase differences between echoes associated with a pulse sequence of the FSE method are not removed but are averaged to disperse them in a k-space, calculation to correct the phase differences; pulse sequence adjustment; etc. are unnecessary, which can remove artifacts easily.

<First Variation>

Figure 9:
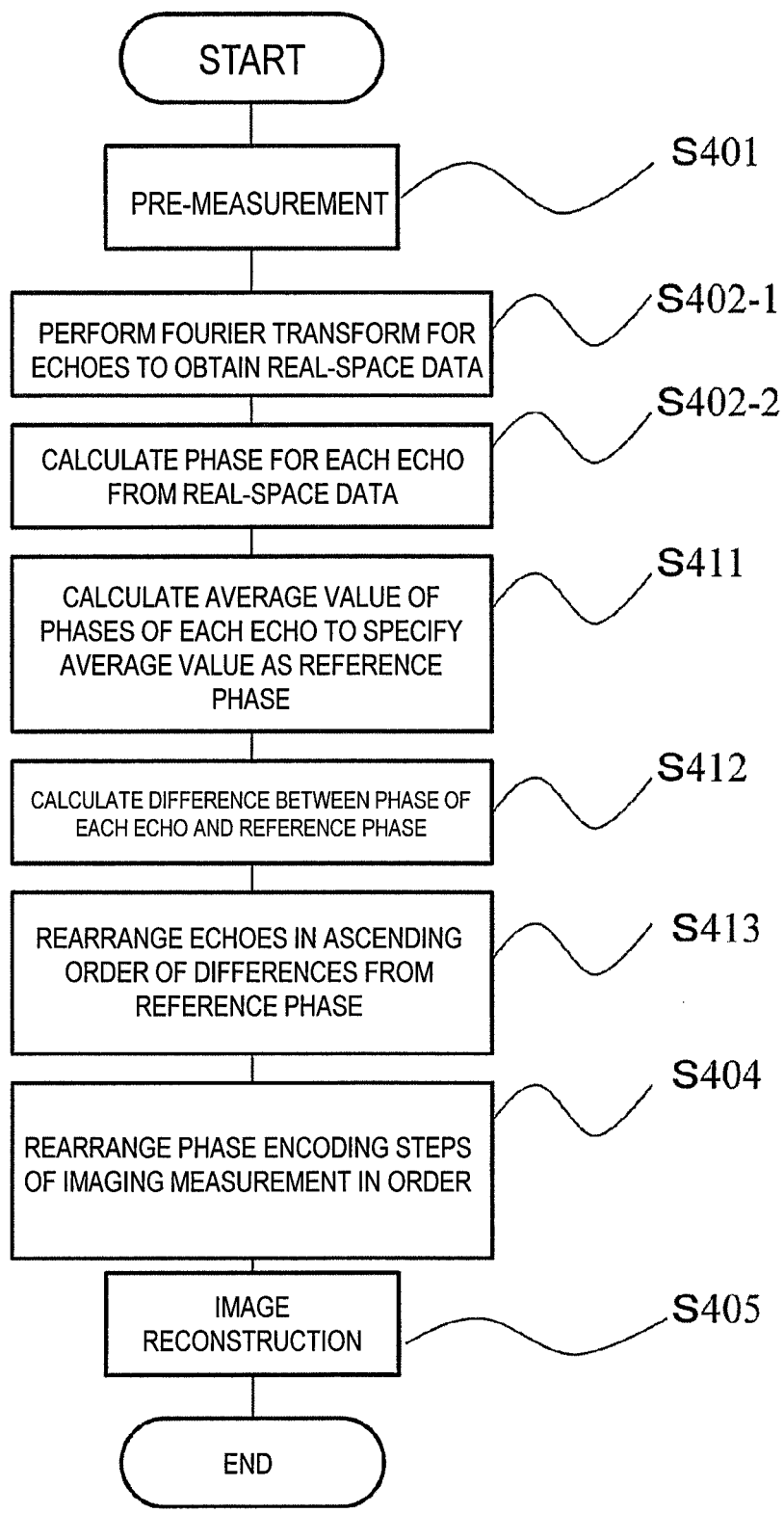
FIG. 9 is a flow diagram showing a processing procedure of the change example 1 of the first embodiment.

In a case where short TE imaging is performed in a pulse sequence of the FSE method, the centric order that disposes an echo obtained first after RF excitation in the center of a k-space is adopted. Also, there are many cases where the above phase difference becomes the largest among all the echoes between an echo obtained first and that obtained second. Therefore, in the first embodiment, the case where an arrangement order is controlled on the centric-order basis was described. However, the present embodiment, without limiting to the centric order, can apply also to the other arrangement orders. In this case, the phase of the first echo is not specified as a reference, but an arbitrary echo that disposed in the center of a k-space can be specified as a reference. Also, an average value of phases of multiple echoes may be specified as a reference. The procedure in a case where an average value of phases of multiple echoes is specified as a reference phase is shown in FIG. 9. In FIG. 9, the steps with the same processing contents as FIG. 4 are denoted by the same numerals.

Similarly to imaging measurement, performing pre-measurement using a pulse sequence without phase encoding to obtain multiple echoes and performing the Fourier transform for these echoes to calculate phases are the same as Steps S401, S402-1, and S402-2 in FIG. 4. Next, an average of the respective echoes is calculated, and the average value is specified as a reference value (Step S411). Differences between phases of the respective echoes and the reference phase are calculated (Step S412). Then, the respective echoes are arranged in an ascending order of phase differences from the reference phase (Step S413). This order is to be the arranging order in a k-space. For example, if an echo whose phase difference from the reference phase is the smallest in the pre-measurement is the second echo, phase encoding is configured so that an echo to be collected second after RF excitation in a pulse sequence of imaging measurement is disposed in the center of the k-space. Phase encoding is configured so that an echo whose phase difference is the next smallest is adjacent to the second echo in the k-space. Hereinafter, according to the order of the arranged echoes in Step S413, phase encoding is similarly configured so that the echoes are arranged in the k-space.

The Procedure of performing imaging measurement and image reconstruction (S404 and S405) according to the thus-determined arrangement order is the same as the first embodiment.

In this variation, although an echo to be measured first is not necessarily disposed in the center of a k-space, the effect of suppressing an image blur by averaging phase errors is obtained similarly. Additionally, in this variation, a condition where the first echo is disposed in the center of a k-space in arrangement order control of the k-space can also be added.

In the first embodiment, although the description was performed without distinguishing whether the pulse sequence in FIG. 2 is the single shot or multi-shot, in the second variation, a case of the multi-shot where all the multiple echoes filled in the whole k-space is collected not after one excitation but in multiple excitations will be described. In case of the multi-shot, although phase encoding needs to be configured for each shot, it is OK to perform pre-measurement once, and the procedure of determining an arrangement order of echoes in light of phase characteristics of the echoes obtained by the pre-measurement is the same as the first embodiment.

In the multi-shot, in case of the centric order, while a measurement start position in a k-space is being shifted for each shot, the measurement is generally performed for each shot from the center side to the high-frequency side in the k-space.

Figure 10:
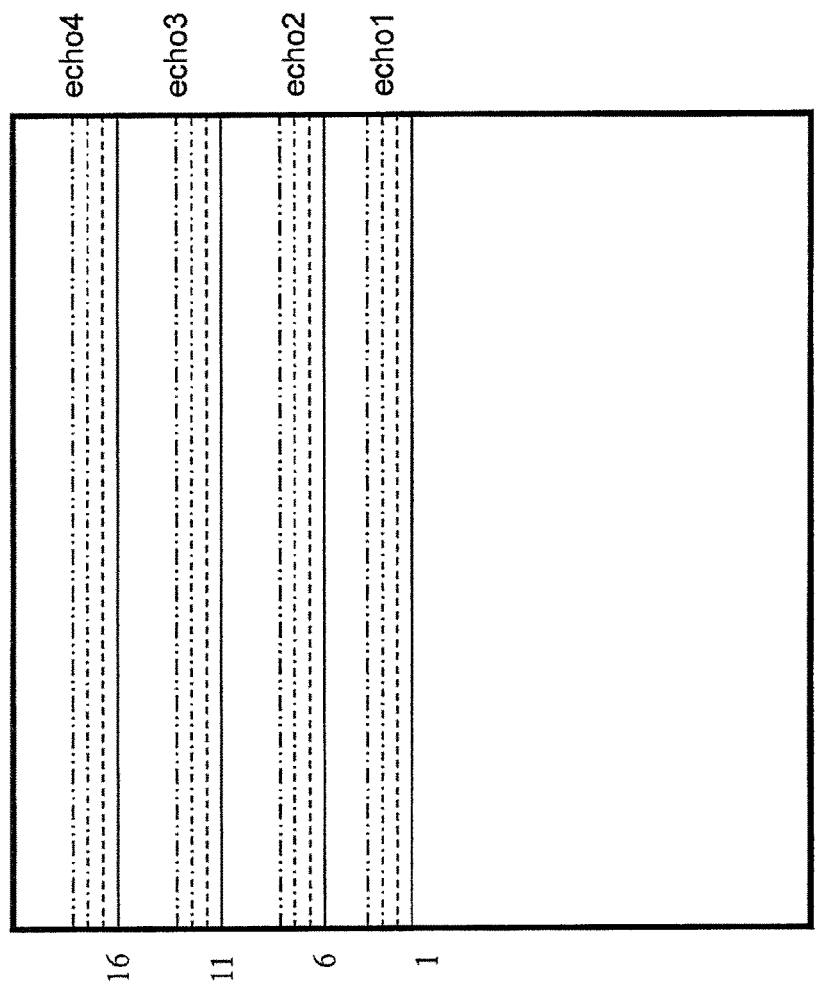
FIG. 10 is a diagram showing an example of k-space division when multi-shot imaging is performed.

For example, as shown in FIG. 10, echoes in the phase encodings 1, 6, 11, . . . are measured in a first shot, echoes in the phase encodings 2, 7, 12, . . . are measured in a second shot, and echoes in the phase encodings 3, 8, 13, . . . are measured in a third shot. In the diagram, the echoes collected in the same shot are shown with the same line type. In such a case, although multiple echoes measured in one shot are to be arranged at intervals of multiple echoes without being adjacent to each other in a k-space (at intervals of five echoes in the above-mentioned example), it may be controlled so that the echoes are arranged according to the arrangement order determined in light of phase characteristics of the respective echoes in Step S403 (or Step S413).

Therefore, among echoes in the phase encodings 1, 6, and 11 to be obtained a first shot, for example, the first echo is specified as the phase encoding 1, the phase encoding of an echo (for example, the k-th echo) whose phase difference from the first echo is the smallest is specified as 6, and the phase encoding of an echo (for example, the m-th echo) whose phase difference is the next smallest is specified as 11. Similarly also to the second shot, the phase encodings of the first, k-th, m-th, . . . echo are specified as 2, 7, 12, . . . respectively, and also in the third shot, the phase encodings of the first, k-th, m-th, . . . echo are specified as 3, 8, 13, . . . respectively.

Additionally, in a case where measurement is performed by dividing the measurement region in a k-space for each shot, only an offset amount of phase encoding is changed for each shot, and similarly to a case of the single shot, the phase encoding may be controlled according to the arrangement order determined in Step S403 (or Step S413). For example, in a case where ten echoes of the phase encodings 11 to 20 are measured in a second shot after ten echoes of the phase encodings 1 to 10 are measured in a first shot, an increment operation is performed serially for the phase encodings in an order where the first to tenth echoes are rearranged (an order in which the first is the top) in both the respective shots.

Additionally, in FIG. 10, although data of a region on the negative side in the phase encoding direction from the center of the k-space is omitted, controlling an echo arrangement order also in the region is similar to the above.

Second Embodiment

In the present embodiment, phase characteristics of the respective echoes are not obtained by pre-measurement, but previously known phase characteristics or those peculiar to a pulse sequence of the FSE method are used to control a k-space arrangement order. The control of the arrangement order of echoes into the k-space is performed via controlling an application amount of a phase encoding gradient magnetic field. That is, a control unit, as phase characteristics of multiple echoes, uses phase characteristics of echoes to be collected at odd-number orders and echoes to be collected at even-number orders after RF excitation to control the k-space arrangement order. For example, of the echoes to be collected at odd number orders and the echoes to be collected at even-number orders, ones are arranged in a first region that includes the center of the k-space or that is adjacent to the center, and the others are arranged in a second region that is located on the high-frequency side of the first region.

Although the configuration of the control unit is similar to the functional block diagram of FIG. 5, can be omitted the phase-characteristics obtaining unit including the pre-measurement control unit 81 and the phase calculation unit 82.

In a pulse sequence of the FSE method, it is known that there is a difference of the character "even echo rephasing" between an odd-numbered echo (hereinafter, simply referred to as an odd echo) and an even-numbered echo (hereinafter, simply referred to as an even echo) after RF excitation. The characteristic difference is generated between odd echoes and even echoes by an RF pulse, a magnetic field error of a read-out magnetic field, etc. being cancelled when even echoes are converged. A large difference appears particularly between a first echo and a second echo. In the present embodiment, in light of phase characteristics peculiar to the pulse sequence of the FSE method, a k-space arrangement order of echoes is performed. A state of control by a control unit is shown in FIG. 11. In FIG. 11, (a) shows a case where the k-space arrangement is performed by general centric ordering, and (b) shows a case where control of the arrangement order is performed by the present embodiment.

As shown in FIG. 11(a), for example, in a case where six echoes measured by one excitation are arranged on the high-frequency side from the center of a k-space in order from the first echo echo1, phase differences shown with the dotted lines in the diagram are generated between odd echoes and even echoes that are different in phase characteristics, and the phase differences are generated for each echo.

In the present embodiment, an arrangement order is controlled so that odd echoes are adjacent to each other and so that even echoes are adjacent to each other. Specifically, echoes of the first, third, fifth, . . . are arranged in order from the center of a k-space, and the second, fourth, sixth, . . . are arranged on the high-frequency side. Although the description is omitted, the arrangement order is similar also to the negative side in the phase encoding direction from the center of the k-space. In this case, although it is highly possible that a larger phase difference than phase differences between odd echoes is generated between the fifth echo and the second echo, the position where the larger phase difference is generated is moved to the high-frequency side compared to the case(a). Then, the low-frequency regions on both sides of the center of the k-space are filled with odd echoes whose phase differences are small. In a case where such k-space data is visualized, an image blur can be substantially removed compared to the k-space data of (a).

According to the present embodiment, image artifacts can be reduced, and additionally, pre-measurement is not required, which can avoid imaging time from being extended by the pre-measurement. Additionally, although the above description describes a case where phase characteristics peculiar to a pulse sequence of the FSE method are used as the phase characteristics to control a k-space arrangement order, any pulse sequences on the basis of the FSE method can be applied.

Also in the present embodiment, as described in the second variation of the first embodiment, a pulse sequence of the FSE method can be applied to either of the multi-shot or the single shot.

Third Embodiment

The present embodiment is characterized by performing control both the arrangement orders in which one is similar to the first embodiment and based on phase characteristics of echoes obtained by pre-measurement; the other is similar to the second embodiment and based on phase characteristics of odd echoes and even echoes.

Also in the present embodiment, as shown in FIG. 6, the pre-measurement pulse sequence similar to a real-imaging pulse sequence without including a phase encoding is performed to obtain multiple echoes. Next, these echoes are separated into odd echoes and even echoes, and differences between the phases and a reference phase are calculated for each echo. As the reference phase, a phase with the smallest echo number (the first echo of the odd echoes and the second echo of the even echoes) may be used, and an average value of multiple odd echoes and an average value of multiple even echoes may also be used. Next, according to the phase difference, echoes are rearranged to determine an arrangement order. For example, in a case where a small echo number is specified as a reference, it is supposed that an echo with the echo number is to be disposed in the center of a k-space or a position closest to the center, and it is supposed that the other echoes are arranged outside in the ascending order of the phase differences.

At this point, similarly to the second embodiment, a k-space region is separated between odd echoes and even echoes.

For example, it is supposed that the odd echoes are arranged in a region including the center of the k-space, and it is supposed that the even echoes are arranged outside the region (on the high-frequency side). The arrangement order of the respective odd echoes and even echoes in this region is configured to be the ascending order of the phase differences from the center to the high-frequency side as described above.

Also in the present embodiment, a boundary between an odd echo and an even echo where the phase difference becomes the largest can be moved to the high-frequency side from the k-space center, and additionally, echoes are arranged in an arrangement order where the phase difference is the smallest between echoes in the central region of the k-space, which can further improve the effect to prevent an image blur.

Fourth Embodiment

In the diagrams (FIGS. 2 and 6) used to describe the first and second embodiments, as a pulse sequence of the FSE method, the 2D pulse sequence is shown, but in the present embodiment, a case of radial scanning will be described.

Figure 12:
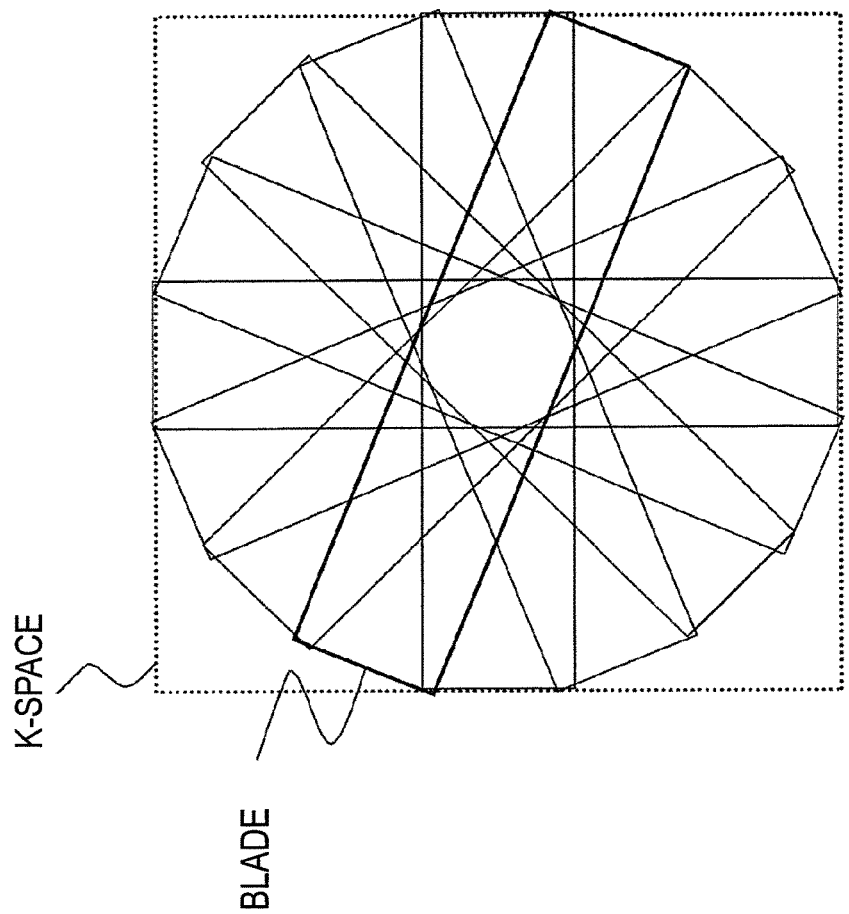
FIG. 12 is a diagram showing a k-space arrangement by the fourth embodiment.

In case of the FSE method even in a pulse sequence of radial scanning (or hybrid radial scanning), although measuring multiple echoes by spin flip using a 180-degree pulse after a single RF excitation is similar to a normal (rectangular) pulse sequence, as shown in FIG. 12, in order to scan a k-space radially, the multiple echoes are measured while gradient magnetic fields in the phase encoding direction and the frequency encoding direction are being changed respectively for each echo. Here, a small region referred to as "blade" is comprised of multiple echoes with a same angle to the axes in a k-space, makes a ratio of the phase encoding gradient magnetic field and the frequency encoding gradient magnetic field constant, and performs measurement by changing the respective offset values for each echo, which can collect the multiple echoes comprising a blade. In a case where radial scanning including such a blade is executed using the FSE method, the multiple echoes comprising one blade in one excitation are measured. Therefore, the number of echo trains is the same as the number of echoes of the blade.

In the present embodiment, an arrangement order of echoes comprising one blade is controlled so that mutual phase differences become the smallest. Also in this case, any of a method (the first embodiment) obtaining phase characteristics of each echo by pre-measurement and a method (the second embodiment) using phase characteristics peculiar to the FSE method may be adopted. In case of obtaining the phase characteristics by pre-measurement, an arrangement order of echoes determined by the result after the pre-measurement is performed at one blade angle (for example, the angle 0) may be applied to all the blades in imaging measurement, and alternatively, echo rearrangement (arrangement order control) may be performed for each angle after the pre-measurement is performed for blades at each angle. Which one is to be adopted is a trade-off between shortening measuring time and image quality improvement.

The method to determine an arrangement order of echoes from the pre-measurement result is similar to the method described in the first embodiment and the first variation. After an average value of an echo phase obtained by the pre-measurement is calculated to specify a reference phase, or after the first echo phase is specified as a reference phase, phase differences of each echo are calculated for the reference phase. An arrangement order of echoes of the first to the n-th is determined in the ascending order of the phase differences, and the arrangement order is the one in which the echoes are arranged from one end toward the other end of the blade.

In imaging measurement, according to the determined arrangement order, a gradient magnetic field step (an increment) to be provided for each shot and each echo is controlled, and it is configured so that echoes of the first to the n-th are arranged in the blade region.

Also in the present embodiment, it is controlled so that a phase difference of each echo in the blade becomes the smallest, which can prevent an image blur caused by the phase difference.

<User Interface>

Next, an example of a graphical user interface (GUI) that can be applied to each embodiment of the present invention described above will be described.

An MRI apparatus to achieve the present GUI includes a user interface unit in which a control unit receives a command from a user, and the user interface unit includes a control/uncontrol selection unit that enables a user to select whether to control a k-space arrangement order by the control unit. Also, the user interface unit can include a phase-characteristics selection unit that selects whether to use a specified value or whether to use phase characteristics obtained by pre-measurement as phase characteristics of multiple echoes.

Figure 13:
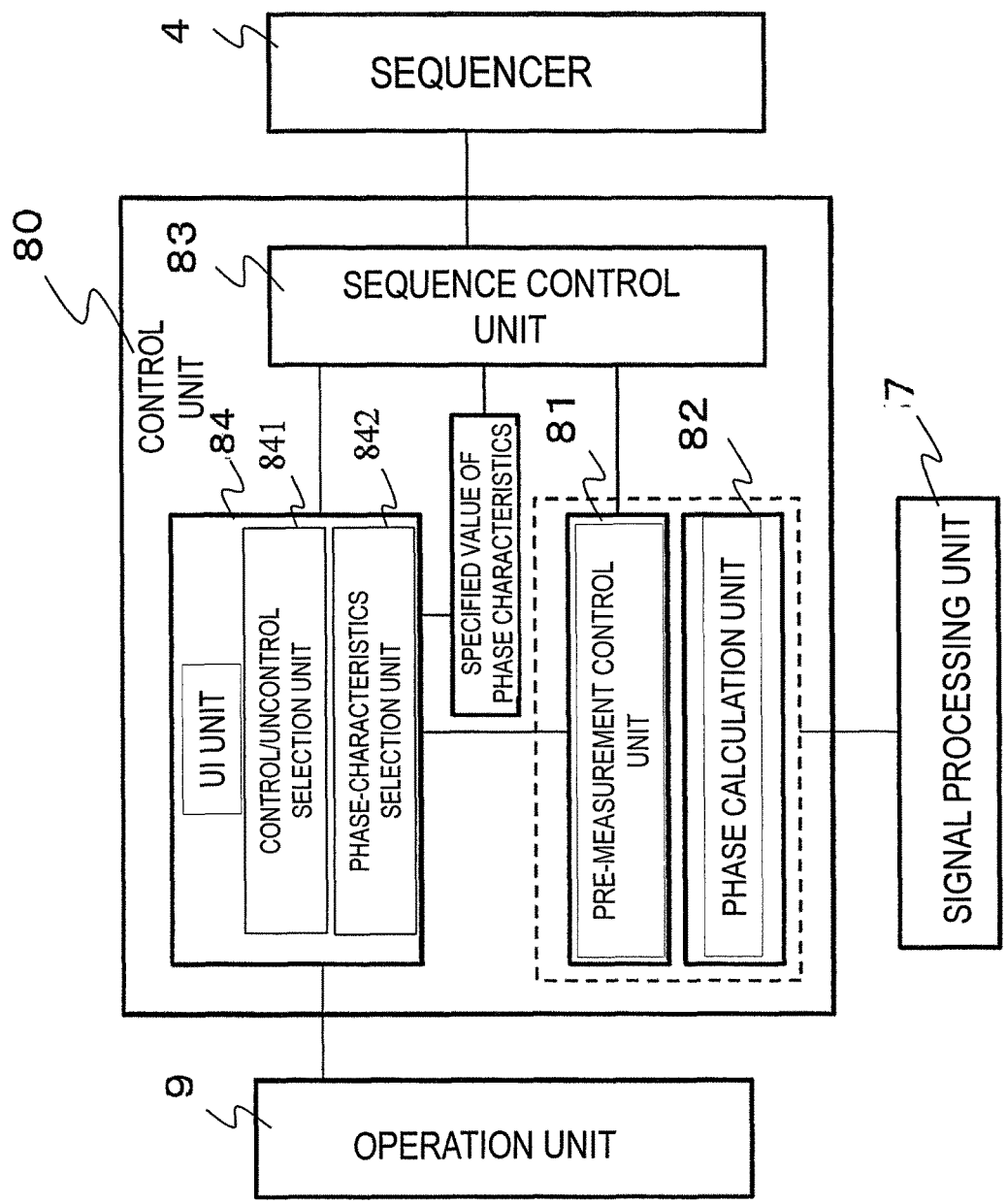
FIG. 13 is a functional block diagram of the fifth embodiment.

The functional block diagram of a control unit of an MRI apparatus of the present embodiment will be shown in FIG. 13. As shown in the diagram, the control unit, similarly to that shown in FIG. 5, is comprised of the pre-measurement control unit 81, the phase calculation unit 82, the sequence control unit (arrangement order control unit) 83, and the user interface unit (UI unit) 84, and additionally, the UI unit 84 is comprised of the control/uncontrol selection unit 841 and the phase-characteristics selection unit 842. The functions of the pre-measurement control unit 81, the phase calculation unit 82, and the sequence control unit 83 are similar to the first embodiment. The control/uncontrol selection unit 841 is a tool (a press button, a check box, etc.) that enables a user to select whether to control an arrangement order on the UI, and the phase-characteristics selection unit 842 is a tool (a press button, a check box, etc.) that enables users to select whether to use a predetermined specified value or obtain phase characteristics by pre-measurement in case of controlling an arrangement order.

Figure 14:
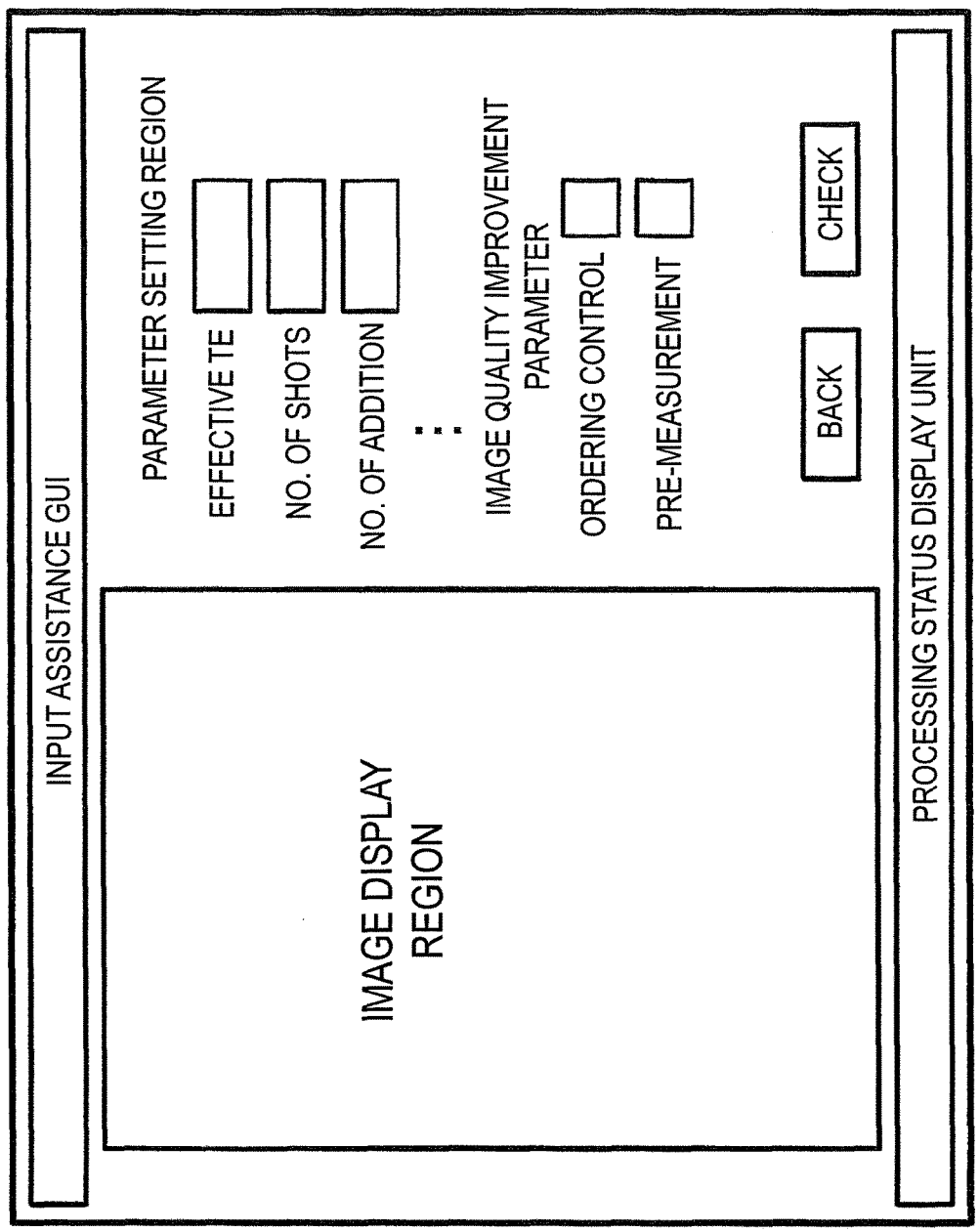
FIG. 14 is a diagram showing an example of the screen on a display unit by the fifth embodiment.

An example of the screen on the display unit after a pulse sequence by the FSE method is selected is shown in FIG. 14.

When a pulse sequence is set as shown in the diagram, an input screen of parameters that can be set by a user is displayed. The parameters include an effective echo time (TE), the number of shots, and an image quality improvement parameters. As one of the image quality improvement parameters, either of effective TE prioritization or ordering control can be selected. In a case where the ordering (k-space arrangement order) control is performed, an effective TE appearing in an image can change, therefore, an undesirable contrast change may occur depending on the contrast type of the image. A user determines and selects whether the effective TE is prioritized or whether image quality improvement by ordering control is prioritized via GUI.

It may be configured to further select whether pre-measurement is required or not in a case where ordering control is selected. As already described, whether pre-measurement is performed or not is a trade-off between avoiding imaging time extension and image quality improvement, a user select it in light of this. Alternatively, it can be configured so that a user can change after either one is set by default.

According to the present embodiment, GUI in which k-space arrangement order control and the contents of the present invention can be selected by a user is provided, which enables a user to select the k-space arrangement order control in light of an imaging target and a purpose of imaging.

The main embodiments of an MRI apparatus of the present invention were described above, and the main characteristics of the MRI apparatus of the present invention are as follows.

A control unit executing a pulse sequence of the FSE method uses phase characteristics of multiple echoes to be collected after a single RF excitation to control an arrangement order in a k-space where the multiple echoes are arranged. The phase characteristics of the multiple echoes may be measured by a pre-measurement unit, and phase characteristics peculiar to odd echoes and even echoes from among the multiple echoes may be used.

The k-space arrangement order control that uses phase characteristics by pre-measurement, for example, calculates a difference between a reference phase and phases of multiple echoes obtained by the pre-measurement, rearranges the multiple echoes in the ascending order of phase differences from the reference phase, and determines the order as an arrangement order. As the reference phase, a phase of an echo to be collected first after RF excitation can be used, and an average value of phases of multiple echoes to be collected after a single RF excitation can also be used.

In an MRI apparatus of the present invention, ideally, a control unit disposes an echo to be collected first after RF excitation in the center of a k-space. This arrangement control is k-space arrangement for which the centric order was corrected.

In the arrangement control that utilizes phase characteristics of odd echoes and even echoes, a k-space is separated into multiple regions, either one of the odd echoes or even echoes are arranged in a first region that includes the center of the k-space, and the other echoes are arranged in a second region located on the high-frequency side of the first region.

Pulse sequences of the FSE method that an MRI apparatus of the present invention include a 2D pulse sequence, a 3D pulse sequence, a radial pulse sequence, and a pulse sequence in which a known pre-pulse is added to those.

An MRI apparatus of the present invention further includes a user interface unit receiving a command from a user, and the user interface unit includes a control/uncontrol selection unit enabling a user to select control of a k-space arrangement order by a control unit. Additionally, in a case where control of the k-space arrangement order is selected, a phase-characteristics selection unit selecting whether to obtain phase characteristics of multiple echoes required for the control by pre-measurement or whether to use a specified value is provided.

INDUSTRIAL APPLICABILITY

According to the present invention, image quality can be improved in a pulse sequence by the FSE method. Although a magnetic field error for each echo cannot be coped with by a normal pulse sequence adjustment, the present invention can particularly solve an influence (blur) that such an error causes in image quality.

DESCRIPTION OF REFERENCE NUMERALS

1: object, 2: static magnetic field generation magnetic circuit, 3: gradient magnetic field generating unit, 4: sequencer, 5: transmission unit, 6: reception unit, 7: signal processing unit, 8: central processing unit (CPU), 9: operation unit (user interface unit)

The invention claimed is:

1. A magnetic resonance imaging apparatus comprising:
a high frequency magnetic field generating unit to generate a high-frequency magnetic field in a static magnetic field space;
a gradient magnetic field generating unit to generate a gradient magnetic field in the static magnetic field space;
a reception unit to receive a nuclear magnetic resonance signal generated from an examination target placed in the static magnetic field space;
a control unit to control the high-frequency magnetic field generating unit, the gradient magnetic field generating unit and the reception unit, to execute a pulse sequence of the fast spin echo method that collects multiple echoes using a spin flip after a single RF excitation, and to control an arrangement order in a k-space where the multiple echoes are arranged based on phase characteristics of the multiple echoes collected after the single RF excitation; and
a phase calculation unit to calculate, as the phase characteristics, phase differences between a reference phase and phases of the multiple echoes, and to determine the arrangement order according to the phase differences;
wherein the control unit arranges the multiple echoes measured in the pulse sequence of the fast spin echo method in the k-space, according to the arrangement order determined by the phase calculation unit.

2. The magnetic resonance imaging apparatus according to claim 1, comprising:
a pre-measurement unit to measure the phase characteristics of the multiple echoes.

3. The magnetic resonance imaging apparatus according to claim 2, comprising:
the phase calculation unit determines the arrangement order in the ascending order of the phase differences.

4. The magnetic resonance imaging apparatus according to claim 3,
wherein the control unit disposes an echo to be collected first after the single RF excitation in a center of the k-space or a position close to the center, and arranges second and subsequent echoes in the k-space according to the arrangement order determined by the phase calculation unit.

5. The magnetic resonance imaging apparatus according to claim 3,
wherein the reference phase is a phase value of an echo collected first after the single RF excitation.

6. The magnetic resonance imaging apparatus according to claim 3, wherein the reference phase is an average value of phases of multiple echoes collected after the single RF excitation.

7. The magnetic resonance imaging apparatus according to claim 1,
wherein the control unit uses phase characteristics of echoes collected at odd-number orders and echoes collected at even-number orders after the single RF excitation, to control the arrangement order.

8. The magnetic resonance imaging apparatus according to claim 7,
wherein the control unit arranges, of the echoes collected at odd number orders and the echoes collected at even-number orders, ones in a first region that includes the center of a k-space, and the others in a second region that is located on a high-frequency side of the first region.

9. The magnetic resonance imaging apparatus according to claim 1,
wherein a pulse sequence of the fast spin echo method includes at least one of a 2D pulse sequence, a 3D pulse sequence, and radial pulse sequence.

10. The magnetic resonance imaging apparatus according to claim 1,
wherein the control unit has a user interface unit to receive a command from a user, and the user interface unit has a control/uncontrol selection unit that enables a user to select whether to control a k-space arrangement order by the control unit.

11. The magnetic resonance imaging apparatus according to claim 10,
wherein the user interface unit has a phase-characteristics selection unit to select whether to use a specified value or whether to use phase characteristics obtained by pre-measurement, as phase characteristics of the multiple echoes.

12. The magnetic resonance imaging apparatus according to claim 1,
wherein the control unit controls an application amount of a phase-encoding gradient magnetic field to control an arrangement order of echoes in the k-space.

13. A magnetic resonance imaging method in a magnetic resonance imaging apparatus imaging using a pulse sequence of the fast spin echo method that collects multiple echoes using a spin flip after a single RF excitation, the method comprising:

generating a high-frequency magnetic field in a static magnetic field space, via a high frequency field generating unit;

generating a gradient magnetic field in the static magnetic field space, via a gradient magnetic field generating unit;

receiving a nuclear magnetic resonance signal generated from an examination target placed in the static magnetic field space, via a reception unit;

controlling the high-frequency magnetic field generating unit, the gradient magnetic field generating unit and the reception unit, via a control unit, to execute a pulse sequence of the fast spin echo method that collects multiple echoes using a spin flip after a single RF excitation, and to control an arrangement order in a k-space where the multiple echoes are arranged based on phase characteristics of the multiple echoes collected after the single RF excitation; and calculating, as the phase characteristics, phase differences between a reference phase and phases of the multiple echoes, and determining the arrangement order according to the phase differences;

wherein the controlling arranges the multiple echoes measured in the pulse sequence of the fast spin echo method in the k-space, according to the arrangement order determined by the determining.

\* \* \* \* \*